United States Patent
Li et al.

(10) Patent No.: US 8,802,014 B2
(45) Date of Patent: Aug. 12, 2014

(54) GA-68 RADIONUCLIDE GENERATOR STRUCTURE

(75) Inventors: Ming-Hsin Li, Taoyuan County (TW); Jin-Jenn Lin, Taoyuan County (TW); Ther-Jen Ting, Taoyuan County (TW); I-Lea Dai, Taoyuan County (TW)

(73) Assignee: Institute of Nuclear Energy Research, Jiaan Village, Longtan, Taoyuan (TW)

( * ) Notice: Subject to any disclaimer, the term of this patent is extended or adjusted under 35 U.S.C. 154(b) by 186 days.

(21) Appl. No.: 13/252,195

(22) Filed: Oct. 3, 2011

(65) Prior Publication Data

US 2013/0084220 A1  Apr. 4, 2013

(51) Int. Cl.
*G21G 4/08* (2006.01)
*G21G 1/00* (2006.01)

(52) U.S. Cl.
CPC ............... *G21G 4/08* (2013.01); *G21G 1/0005* (2013.01); *Y10S 422/903* (2013.01); *G21G 2001/0021* (2013.01)
USPC ............ 422/159; 422/130; 422/903; 210/682

(58) Field of Classification Search
CPC .................. G21G 1/0005; G21G 2001/0021; G21G 4/08; Y10S 422/903
USPC ........................... 422/159, 130, 903; 210/682
See application file for complete search history.

(56) References Cited

U.S. PATENT DOCUMENTS

| | | | |
|---|---|---|---|
| 6,517,811 B2 * | 2/2003 | John et al. | 424/1.81 |
| 7,728,310 B2 * | 6/2010 | Fitzsimmons et al. | 250/432 PD |
| 2008/0277350 A1 * | 11/2008 | Roesch et al. | 210/682 |

* cited by examiner

*Primary Examiner* — Lessanework Seifu

(57) ABSTRACT

The invention is related a novel structure for Ga-68 radionuclide generator. It allows two washing solutions to pass through two Ge-68 absorbents to wash out different chemical forms of Ga-68 nuclide. The invention comprises the first method that will withdraw hydrochloric acid solution from the washing bottle and pass it through inorganic resin absorbing column to produce the radioisotope solution of Ga-68 gallium chloride, and the second method that will allow the radioisotope solution of Ga-68 gallium citrate to pass the organic resin absorbing column and then the silica-gel cartridge, and be washed by the hydrochloric acid solution to obtain the radioisotope solution of Ga-68 gallium chloride.

7 Claims, 2 Drawing Sheets

US 8,802,014 B2

GA-68 RADIONUCLIDE GENERATOR STRUCTURE

BACKGROUND OF THE INVENTION

1. Field of the Invention

The invention is related to a novel structure for a Ga-68 radionuclide generator that uses two washing solutions to pass through two Ge-68 absorbents to wash out different chemical forms of Ga-68 nuclide.

2. Description of the Prior Art

Because parent nuclide Ge-68 has long half-life, Ge-68/Ga-68 nuclide generator can be used for more than one year to steadily provide Ga-68 nuclide.

In the past, Ge-68 is adsorbed on inorganic materials like silicon dioxide, aluminum oxide or tin oxide to produce Ga-68 nuclide generator. With these materials, there is inevitably inconvenience. For example, if a generator uses aluminum oxide as adsorption column, it will need EDTA (ethylediaminetetraacetic acid) solution to wash out daughter nuclide Ga-68. Since Ga-68-EDTA is a complex with very stable structure, it takes some complicated processes to convert Ga-68 into radiopharmaceuticals. Also because Ga-68 has short half-life, the conversion process will lose some materials. If a generator uses tin oxide as adsorption column, it will need 1N HCl solution or more concentrated to wash out daughter nuclide Ga-68. Thus, Ga-68 nuclide exists as chlorinated Ga and can be used after neutralization. However, the trace amount of inorganic salt can be dissolved and carried out by a strong acid(HC1 concentration >1N) and easily cause metal ion contamination. Its convenience lies in the further labeling for Ga-68 with ligand.

The Ga-68 nuclide generators that are made from adsorption of Ge-68 in silicon dioxide, aluminum oxide or tin oxide have the following common features: (1) existing as a form of strong acid solution (HCl concentration>1N), (2) easily causing ion metal contamination, (3) if the chemical form of Ga-68-gallium citrate is needed, it is more time consuming and is not suitable for pharmaceutical production or clinical use because the exposure of operators to radiation is higher, (4) if Ga-68 nuclide exists as gallium chloride, it cannot be directly used for clinical purpose and needs further labeling for Ga-68 nuclide with ligand.

The Ga-68 nuclide generator that is made from adsorption of Ge-68 in organic resins has the following features: (1) it needs diluted sodium citrate or sodium phosphate solution to wash Ga-68 nuclide, (2) it exists as Ga-68-gallium citrate, (3) it does not cause ion metal contamination, (4) if the chemical form of Ga-68-gallium chloride is needed, it is more time consuming and is not suitable for pharmaceutical production or clinical use because the exposure of operators to radiation is higher.

Ga-68 nuclide has found increasing applications in PET radiopharmaceuticals. Single ion form of Ga-68 nuclide generator is not sufficient to meet the demand of diversified development of Ga-68 applications in radiopharmaceuticals. In review of existing literatures and patents, such as U.S. application Ser. No. 12/745,715, which from Fe (III) conducts purification with automatic apparatus to produce single chemical form of Ga-68 nuclide; or another U.S. publication 60/928,723, which uses washing solution and adsorption column for multiple purification operation to produce single chemical form of Ga-68 nuclide, it is found that there is no example like this invention that adopts a process to combine two different washing solutions and two different adsorption columns to obtain different chemical forms of Ga-68 nuclide, i.e. Ga-68-gallium citrate and Ga-68-gallium chloride.

SUMMARY OF THE INVENTION

The objective of the invention is to propose a novel Ga-68 radionuclide generator structure, which uses two washing solutions to pass through two Ge-68 adsorbent to wash out different chemical forms of Ga-68 nuclide for Ge-68/Ga-68 nuclide generator.

Since Ga-68 nuclide has found increasing applications in PET radiopharmaceuticals, single ion form of Ga-68 nuclide generator is not sufficient to meet the demand of diversified development of Ga-68 applications in radiopharmaceuticals. Besides, there is no similar example in existing literatures and patents to this invention that uses two washing solutions to pass two Ge-68 adsorbents to wash out different chemical forms of Ga-68 nuclide for novel Ge-68/Ga-68 nuclide generator. Ga-68 gallium citrate solution or Ga-68 gallium chloride solution can be chelated with chelating agent DotA (1,4,7,10-tetraazacyclododecane-1,4,7,10-tetraacetic acid) as radioisotope solution.

The invention, by using organic resins to absorb Ge-68 and using diluted sodium citrate or sodium phosphate to wash out Ga-68 nuclide, can minimize metal ion contamination. Although Ga-68 nuclide, when exists as gallium citrate, has narrower application range than Ga-68-gallium chloride, its advantage is less metal ion content, which total Ge-68 is approximately 0.0004%.

In addition, Ga-68 nuclide is suitable for PET (Positron Emission Tomography) in radiopharmaceutical molecular labeling, such as application in tumor imaging and diagnostics via crosslink with ligand or peptide or protein and forming covalent bonding.

Since Ga-68 is the daughter nuclide from the decay of Ge-68. Ge-68 has a half-life for as long as 271 days, maximum energy 511 KeV. It is produced via cyclotron irradiation to Ga-69. The nuclear reaction formula is $^{69}$Ga (p,2n)$^{68}$Ge. Ga-68 has a half-life for 68.1 minutes, maximum energy $\beta^+$=1.89 MeV. Since Ga-68 has a short half-life and decays in the form of positron, it is mainly used to prepare positron imaging agent for clinical radiopharmaceuticals and very suitable for hospitals or research institution without cyclotrons.

DETAILED DESCRIPTION OF THE INVENTION

Figure 1:
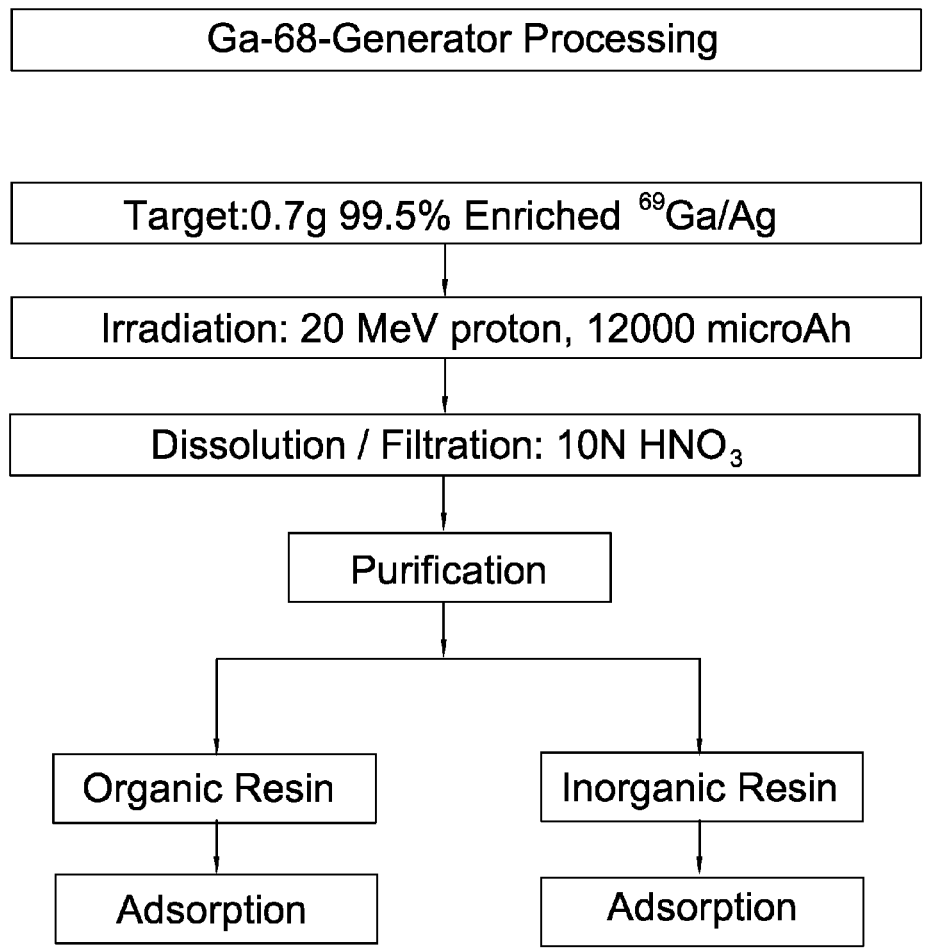
FIG. 1 is the process flow diagram for the operation of the Ga-68 generator in the invention.
Figure 2:
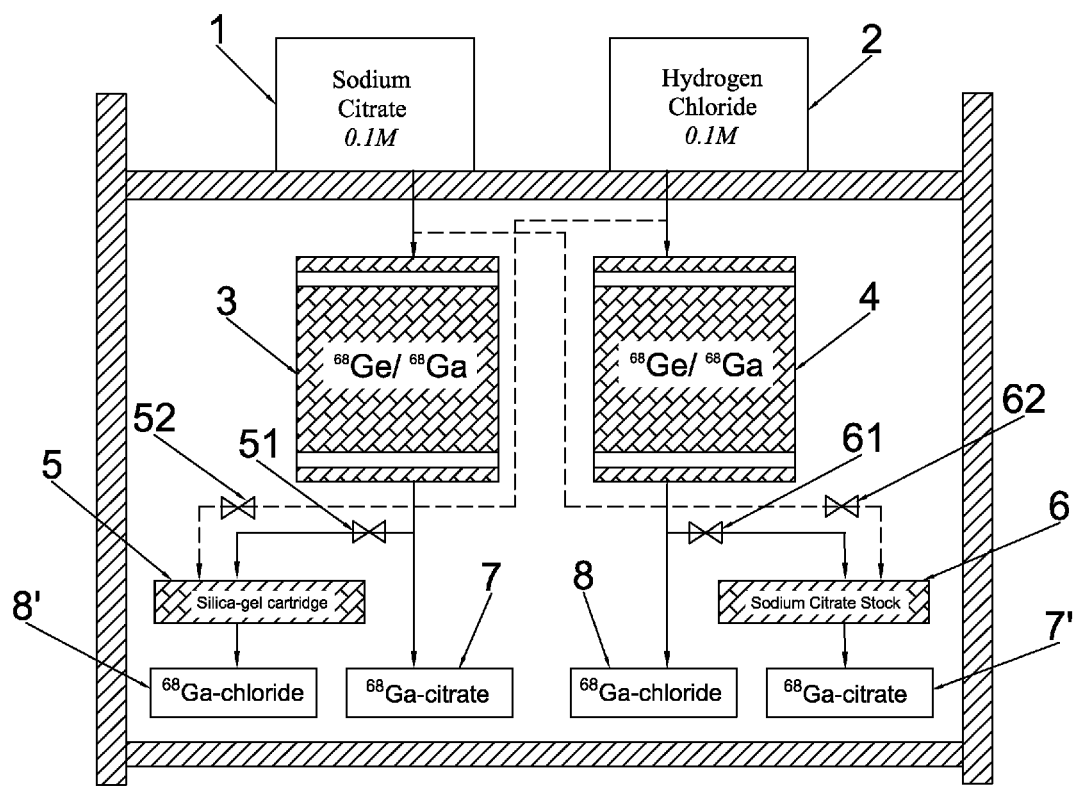
FIG. 2 is the structure diagram for the Ga-68 generator in the invention.

The objective and feature for the invention lies in an operation process that combines two different washing solutions and two different absorbent columns to obtain different chemical forms Ga-68 nuclide, i.e. Ga-68 gallium citrate and Ga-68 gallium chloride. FIG. 1 is the block flow diagram for the operation process of the present invention Ga-68 generator, in which two washing solutions pass through two different Ge-68 absorbents to wash out different chemical forms of Ga-68 nuclide. FIG. 2 has detailed explanation.

As shown in FIG. 2, the present invention structure includes: (1) first washing bottle 1, containing 0.1M sodium citrate stock; (2) second washing bottle 2, containing 0.1M hydrogen chloride stock; (3) organic resin absorbent column 3 (styrene-divinylbenzene copolymer column); (4) inorganic resin absorbent 4 (TiO2 column); (5) silica-gel cartridge 5; (6) sodium citrate stock 6. The two chemical forms of radioisotope solutions from the above method contain (7) radioisotope solution of Ga-68 gallium citrate solution 7 and (8) radioisotope solution of Ga-68 gallium chloride solution 8, which can be used for many different areas such as PET imaging and diagnostics.

Ga-68 gallium citrate can be obtained as shown in FIG. 2. There are two methods. The first is to withdraw the sodium citrate solution from the first washing bottle 1 and allow it to pass through organic resin absorbent column 3, and then drain out radioisotope solution of Ga-68 gallium citrate solution 7; the second is to pass the radioisotope solution of Ga-68 gallium chloride solution 8 through sodium citrate solution 6 to mix, and thus obtain the radioisotope solution of Ga-68 gallium citrate 7'.

Ga-68 gallium chloride can be obtained as in FIG. 2. There are two methods. The first is to withdraw the hydrochloric acid solution from the second washing bottle 2 and allow it to pass through inorganic resin absorbing column 4 to drain out the radioisotope solution of Ga-68 gallium chloride; the second is to pass the radioisotope solution of Ga-68 gallium citrate solution 7 to pass organic resin absorbing column 3 and then silica-gel cartridge 5, followed by washing with the hydrochloric acid solution in the second washing bottle 2 to obtain the radioisotope solution of Ga-68 gallium chloride 8'. Valve 51 and valve 52 in FIG. 2 are open or closed at the same time during operation. Valve 61 and valve 62 are also operatively open or closed at the same time during operation.

What is claimed is:

1. A Ge-68/Ga-68 nuclide generator structure comprising first washing bottle containing sodium citrate solution, second washing bottle containing hydrogen chloride solution, an organic resin absorbing column connected with the first washing bottle, an inorganic resin absorbing column connected with the second washing bottle, a silica-gel cartridge connected with first pair of valves, of which one is connected to the second washing bottle and the other is connected to the organic resin absorbing column, respectively, and sodium citrate stock connected with second pair of valves, of which one is connected to the first washing bottle and the other is connected to the inorganic resin absorbin column, respectively, for producing two chemical forms of radioisotope solution Ga-68 gallium citrate and Ga-68 gallium chloride.

2. According to the structure of Ge-68/Ga-68 nuclide generator described in claim 1, the first washing bottle contains sodium citrate solution at 0.1M; the second washing bottle contains hydrochloric acid solution at 0.1M, wherein concentration of washing solution is determined by the type of washing solution.

3. According to the structure of Ge-68/Ga-68 nuclide generator described in claim 1, first washing device withdrawing the sodium citrate solution and passing through organic resin absorbing column to drain out the radioisotope solution of Ga-68 gallium citrate.

4. According to the structure of Ge-68/Ga-68 nuclide generator described in claim 3, the radioisotope solution of Ga-68 gallium citrate passing silica-gel cartridge through a valve of the first pair of valves and washed in second washing device with hydrochloric acid solution through the other valve of the first pair of valves to obtain the radioisotope solution of Ga-68 gallium chloride, wherein both of the first pair valves are open or closed simultaneously during operation process.

5. According to the structure of Ge-68/Ga-68 nuclide generator described in claim 4, the second washing device withdrawing the hydrochloric acid solution and passing inorganic resin absorbing column to drain out the radioisotope solution of Ga-68 gallium chloride.

6. According to the structure of Ge-68/Ga-68 nuclide generator described in claim 5, the radioisotope solution of Ga-68 gallium chloride passing the sodium citrate stock through a valve of the second pair of valves and mixing with the sodium citrate solution from the first washing bottle through the other valve of the second pair of valves to obtain the radioisotope solution of Ga-68 gallium citrate, wherein both of the second pair valves are open or closed simultaneously during operation process.

7. According to the structure of Ge-68/Ga-68 nuclide generator described in claim 1, the generated radioisotope solution refers to as Ga-68 gallium citrate solution or Ga-68 gallium chloride solution, which can react with chelating agent DotA (1,4,7,10-tetraazacyclododecane-1,4,7,10-tetraacetic acid) to produce chelated radioisotope solution.

\* \* \* \* \*